US007868163B2

(12) United States Patent
Basile et al.

(10) Patent No.: US 7,868,163 B2
(45) Date of Patent: Jan. 11, 2011

(54) ADENYL DINUCLEOTIDES WITH ANTITUMOUR ACTIVITY AND A METHOD OF PREPARING THEREOF

(75) Inventors: Giovanna Basile, Genoa (IT); Umberto Benatti, Genoa (IT); Santina Bruzzone, Genoa (IT); Gianluca Damonte, Arenzano (IT); Antonio De Flora, Genoa (IT); Ernesto Fattorusso, Naples (IT); Luisa Franco, Genoa (IT); Lucrezia Guida, Genoa (IT); Orazio Taglialatela-Scafati, Acerra (IT); Elena Zocchi, Genoa (IT)

(73) Assignees: Universita' Degli Studi Di Genova, Genoa (IT); Centro Biotecnologie Avanzate, Genoa (IT)

( * ) Notice: Subject to any disclaimer, the term of this patent is extended or adjusted under 35 U.S.C. 154(b) by 478 days.

(21) Appl. No.: 11/913,357

(22) PCT Filed: Apr. 28, 2006

(86) PCT No.: PCT/IB2006/051330

§ 371 (c)(1),
(2), (4) Date: Nov. 1, 2007

(87) PCT Pub. No.: WO2006/117735

PCT Pub. Date: Nov. 9, 2006

(65) Prior Publication Data

US 2008/0194509 A1  Aug. 14, 2008

(30) Foreign Application Priority Data

May 2, 2005  (IT) .......................... TO2005A0298

(51) Int. Cl.
*A61K 31/7076*  (2006.01)
*A61K 31/7084*  (2006.01)
*C07H 19/207*  (2006.01)
(52) U.S. Cl. ...................................... 536/27.3; 514/47
(58) Field of Classification Search ....................... None
See application file for complete search history.

(56) References Cited

PUBLICATIONS

Basile et al., ADP-ribosyl cyclases generate two unusual adenine homodinucleotides with cytotoxic activity on mammalian cells PNAS (2005) vol. 102 No. 41, pp. 14509-14514.*
The Merck Manual of Diagnosis and Therapy, published 1999 by Merck Research Laboratories, pp. 397-398, 948-949, 1916, and 1979-1981.*
The Oxford Textbook of Oncology (1995) published by Oxford University Press, pp. 447-453.*
Magnone et al., "Adenylic Dinucleotides Produced by CD38 Are Negative Endogenous Modulators of Platelet Aggregation" The Journal of Biological Chemistry (2008) vol. 283 No. 36, pp. 24460-24468.*

Heal et al., "Optimizing platelet transfusion therapy" Blood Reviews (2004) vol. 18 pp. 149-165.*
Jankowski J et al.; "Dinucleotides as Growth-promoting Extracellular Mediators"; The Journal of Biological Chemistry, Vo. 276, No. 12, Issue of Mar. 23, pp. 8904-8909, 2001.
Luo, J et al.: "Identification and Characterization of diadenosine 5',5'''-P1, P2-diphospate and diadenosine 5',5'''-P1, P3-triphosphate in human myocardial tissue, The FASEB Journal, vol. 13, Apr. 1999, pp. 696-705.
Zocchi, E et al.; The temperature-signaling cascade in sponges involves a heat-gated cation channel, abscisic acid , and cyclic ADP-ribose, PNAS, Dec. 18, 2001, vol. 98, No. 26, pp. 14859-14864.
Zocchi, E et al.; Expression of CD38 Increases Intracellular Calcium Concentration and Reduces Doubling Time in HeLa and 3T3 Cells; The Journal of Biological Chemistry; vol. 273, No. 14, Issue of Apr. 3, pp. 8017-8024, 1998.
Mosmann, Tim; "Rapid Colorimetric Assay for Cellular Growth and Survival: Application and Proliferation and Cytotoxicity Assays", Journal of Immunologic Methods, 65 (1983) pp. 55-63, May 12, 1983.
Graeff, R et al.; "A novel cycling assay for cellular cADP-ribose with nanomolar sensitivity", Biochem J. (2002) 361, 379-384.
Fujiii, T et al, "Systematic Tables of Mono- and Poly-N-Methylated Adenines: Acid Dissociation Constants and UV and NMR Spectral Data", Heterocycles, Vo. 51, No. 9, 1999 pp. 2255-2277.

(Continued)

*Primary Examiner*—Eric S Olson
(74) *Attorney, Agent, or Firm*—Roylance, Abrams, Berdo & Goodman, LLP.

(57) ABSTRACT

The invention relates to novel adenyl dinucleotides which are isomers of the dinucleotide Ap2A, having formulae (I) and (II). The dinucleotides of the invention have antitumour activity, particularly against tumours of haematological origin, such as for example leukaemias and lymphomas. The invention further relates to the use of such dinucleotides as antitumour medicaments. Finally, the invention relates to an enzymatic method for preparing the dinucleotides of formulae (I) and (II) and to an enzymatic assay method for the dinucleotide of formula (I) which is based on its complete conversion to $NAD^+$.

formula I

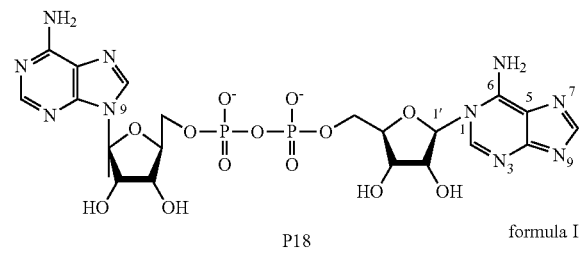

P18 formula II

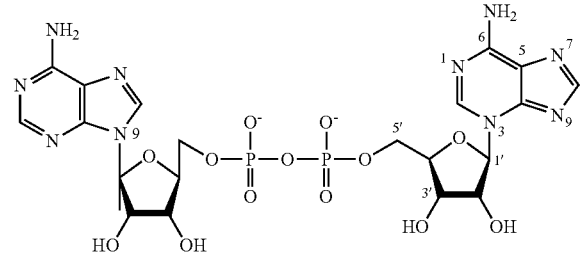

P24

7 Claims, 4 Drawing Sheets

PUBLICATIONS

J. Luo et al.; FASEB Journal, vol. 13, 1999, pp. 695-705, XP002396039.

Joachim Jankowski et al.; Journal of Biological Chemistry, vol. 276, No. 12, 2001, pp. 8904-8909, XP002396040.

Jankowski V et al.; "Isolation and quantification of dinucleoside polyphosphates by using monolithic reversed phase chromatography columns", Journal of Chromatograpyy B: Biomedical Sciences & Applications, Elsevier, Amsterdam, NL, vol. 819, No. 1, May 5, 2005, pp. 131-139, XP004807175.

* cited by examiner

ADENYL DINUCLEOTIDES WITH ANTITUMOUR ACTIVITY AND A METHOD OF PREPARING THEREOF

Field of the Invention

The present invention relates to novel nucleotide compounds with antitumour activity and a method of preparing such compounds by means of an ADP-ribosyl cyclase enzyme.

Background of the Invention

The ADP-ribosyl cyclases (E.C. 3.2.2.5) are a family of enzymes present throughout animal and plant phyla, from protists and unicellular algae to higher Metazoa and Metaphyta. Said enzymes catalyse the synthesis from $NAD^+$ of cyclic ADP-ribose (cADPR), a universal intracellular calcium mobilizer. Cytosolic calcium movements are perhaps the most ancient and universal intracellular signal in cellular physiology. Indeed, ADP-ribosyl cyclases are involved through their product, cADPR, in a number of calcium-dependent cellular functions of increasing complexity from lower Metazoa and Metaphyta to higher animals and plants. The ADP-ribosyl cyclases of lower and higher Metazoa show significant sequence homologies, suggesting that present-day cyclases have evolved from an ancestral, environmental stress-activated enzyme, which is capable of producing a signal molecule active on the cytosolic free calcium concentration ($[Ca^{2+}]_i$).

cADPR is not the only product of ADP-ribosyl cyclase activity: hydrolysis of cADPR, which is catalysed to a variable extent by all the ADP-ribosyl cyclases, produces ADPR which, as has been recently shown to open specific calcium channels on the plasma membrane of various mammalian cell types. Cyclases from lower and higher Metazoa also produce nicotinic acid adenine dinucleotide ($NAADP^+$) by way of a "head exchange reaction" substituting the nicotinamide moiety of $NAD^+$ with nicotinic acid and which takes place only at acidic pH values (pH 4-5). When microinjected into mammalian cells, $NAADP^+$ induces the release of calcium from specific intracellular stores. It is reasonable to suppose that cADPR, ADPR and $NAADP^+$ may cooperate in defining intracellular calcium movements, and the mechanisms modulating the relative concentrations of these calcium agonists are currently the subject of intense research.

The present inventors have now found that the enzymes ADP-ribosyl cyclases are capable of synthesising further molecules in addition to those mentioned above. More particularly, the inventors have found that the ADP-ribosyl cyclases are capable of producing the dinucleotide diadenosine diphosphate (Ap2A), as well as two isomers of Ap2A designated as P18 and P24, respectively, using cADPR and adenine as the substrates.

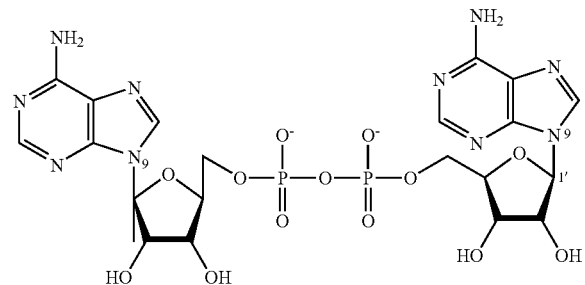

diadenosine diphosphate (Ap2A)

Diadenosine Diphosphate (Ap2A)

The dinucleotide Ap2A had been described previously in platelet secretory granules (Jankowski J., et al. (2001) J. Biol. Chem. 23, 8904-8909) and in cardiac myocytes (Luo J., et al. (1999) FASEB J. 13, 695-705), but the enzyme responsible for its synthesis was unknown. However, the two Ap2A isomers, namely dinucleotides P18 and P24 which are the subject of the invention, were unknown up to now.

The inventors have found that both such dinucleotides contain an unusual N-glycosidic bond between one of the two adenines and a ribose, involving the N1 nitrogen atom in P18 and the N3 nitrogen atom in P24, respectively, as illustrated below in formulae (I) and (II). Thus, dinucleotides P18 and P24 represent the first example of natural dinucleotides containing a glycosidic bond different from the usual N9.

Summary of the Invention

Thus, in a first aspect, the present invention relates to dinucleotide P18 and dinucleotide P24 represented by formulae (I) and (II), respectively:

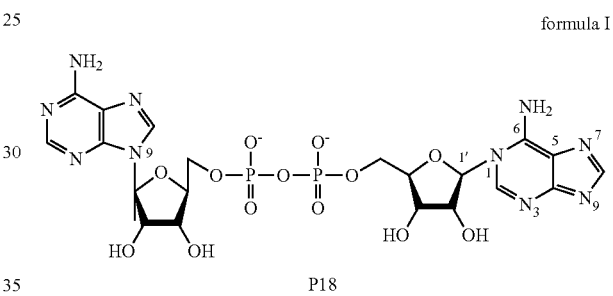

formula I

P18

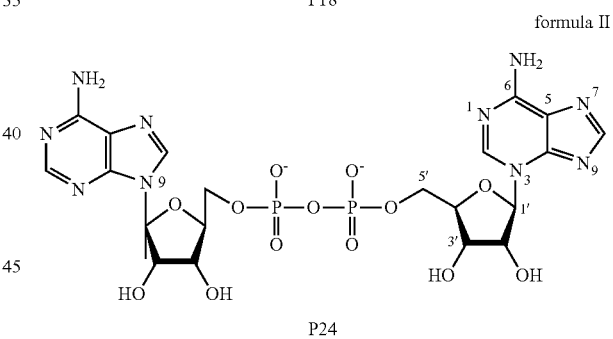

formula II

P24

The above formulae also encompass the salts of compounds P18 and P24, particularly the pharmaceutically acceptable salts of P18 and P24, such as for example sodium, potassium, ammonium and lithium salts.

Another aspect of the invention relates to an enzyme-based reaction for the synthesis of dinucleotides P18 and P24.

In fact, dinucleotides P18 and P24, like Ap2A, can be enzymatically synthesised starting from cADPR (cyclic ADP-ribose) and adenine using an ADP-ribosyl cyclase. The same results can be obtained using $NAD^+$ in replacement of cADPR as the reaction substrate. The inventors have found that the reaction for the synthesis of the P18, P24 and Ap2A dinucleotides takes place by incubating cADPR (or $NAD^+$) and adenine with the enzyme ADP-ribosyl cyclase at a pH value comprised between 6 to 8. Preferably, the pH of the reaction is around neutrality, for example between 7.0 and 7.5. The adenine/cADPR (or adenine/$NAD^+$) stoichiometric ratio is preferably higher than or equal to 10.

As illustrated in further detail below, said enzyme reaction gives rise to a mixture of products comprising Ap2A and the P18 and P24 isomers thereof, each of which, if desired, can then be separated by any suitable method, for example by chromatography, preferably HPLC.

As illustrated in the following experimental section of the description, the inventors have found that the dinucleotides of the invention are present in cyclase-positive animal cells, including human cells. It was further observed that these dinucleotides modify cytosolic free calcium concentrations ($[Ca^{2+}]_i$) when extracellularly applied. Dinucleotide P18 induces a decrease in $[Ca^{2+}]_i$, while dinucleotide P24 induces an increase in $[Ca^{2+}]_i$. The effects of P18 and P24 on cyclase-positive and cyclase-negative human cells were also studied. The results obtained indicate that dinucleotides P18 and P24 inhibit cell proliferation at submicromolar concentrations, both in cyclase-positive and in cyclase-negative cells.

The studies carried out to determine the structures and biological activities of the dinucleotides of the invention will be described in detail in the following experimental sections relating to the "Materials and Methods" and the "Results", with reference to the appended figures in which:

Figure 1:
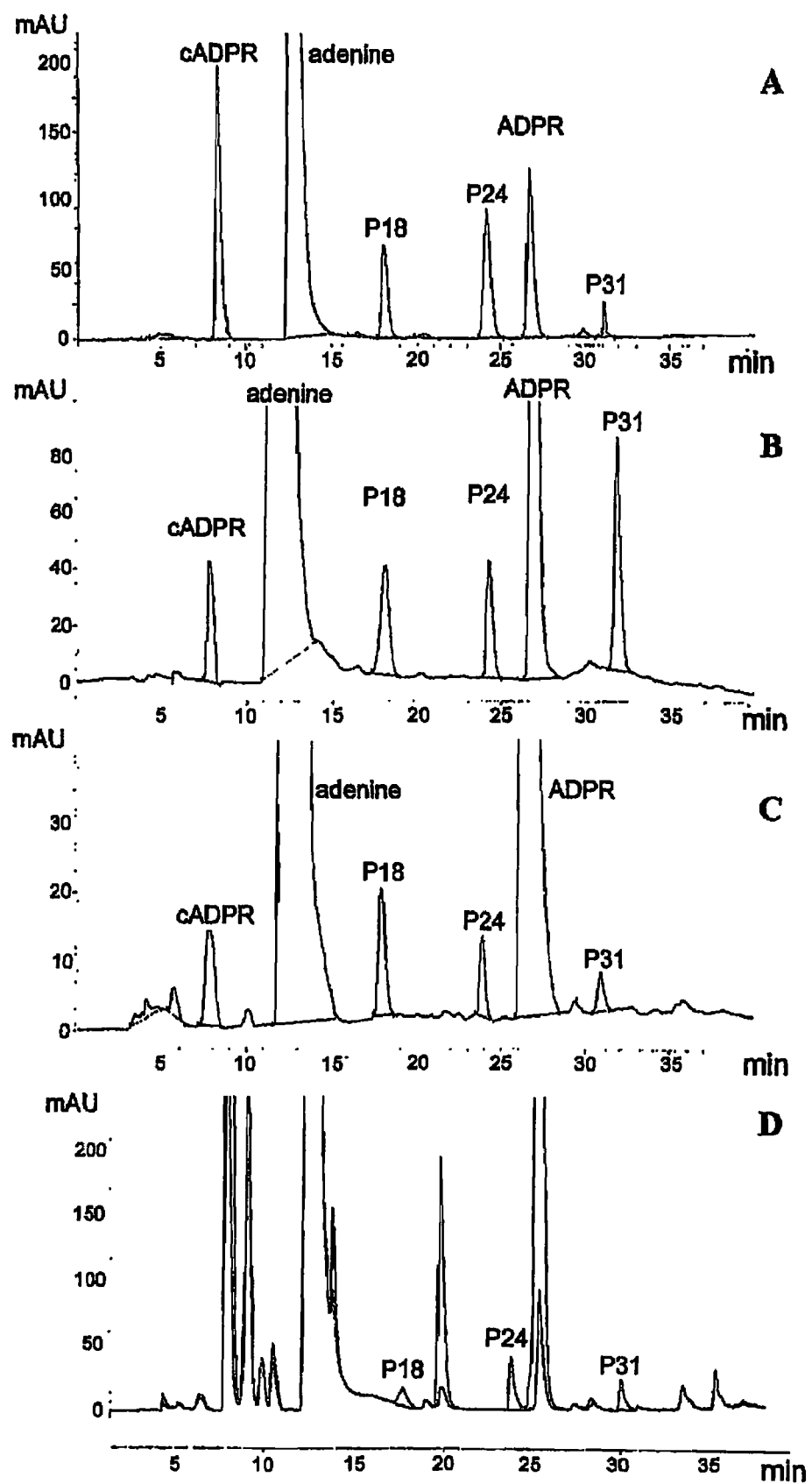
FIG. 1 shows the chromatograms obtained by subjecting cADPR and adenine incubations with ADP-ribosyl cyclases from different sources to HPLC (high performance liquid chromatography). ADP-ribosyl cyclases from lower and higher Metazoa were incubated in the presence of 0.1 mM cADPR and 1 mM adenine at pH 7.4 in 10 mM Tris-HCl (A, B and C) or in PBS-glucose (D) at 22° C. (A and B) or at 37° C. (C and D) for 4 hours. Aliquots of the various incubations were deproteinised with TCA (trichloroacetic acid) and subjected to HPLC (analytical phosphate). Chromatograms representative of each incubation are shown. A. *A. polypoides*; B. *A. californica*; C. Human CD38 (recombinant); D. Human HeLa cells transfected with sense and antisense human CD38 (dashed chromatogram).

The following experimental sections entitled "Materials and Methods" and "Results" are provided by way of illustration only and should not be construed as limiting the scope of the invention, as defined by the appended claims.

Detailed Description of the Preferred Embodiment

EXAMPLES

Materials and Methods

ADP-ribosyl Cyclase

ADP-ribosyl cyclase was purified to electrophoretic homogeneity from the marine sponge *Axinella polypoides* as described in Zocchi, E. et al. (2001) Proc. Natl. Acad. Sci. USA 98, 14859-14864. The cyclase purified from the mollusc *Aplysia californica* was purchased from Sigma. Human HeLa cells transfected with sense (CD38$^+$) and antisense (CD38$^-$) human CD38 were obtained as described in Zocchi E., et al. (1998) J. Biol. Chem. 273, 8017-8024 and were maintained in culture in DMEM medium (Dulbecco's modified Eagle's medium) containing 10% foetal calf serum, penicillin and streptomycin at 37° C. under a 5% $CO_2$ atmosphere.

HPLC Analysis

All HPLC analyses were performed using an Hewlett-Packard (HP 1090) liquid chromatograph with a diode array detector (HP 1040). Analytical phosphate HPLC analysis was performed on a Delta Pak C18 column (150×4 mm, 5 μM, Waters). Solvent A was 0.1 M $KH_2PO_4$ containing 5 mM tetra-n-butylammonium, pH 5.0; solvent B was as solvent A, with 30% (v/v) methanol. The elution gradient increased linearly from 100% A to 100% B over 30 minutes, then remaining at 100% B for 10 minutes; the flow rate was 0.4 ml/minute. Preparative phosphate analysis was performed on a C18 column, 300×7.8 mm, 15 μm (Waters): the buffers and the gradient were as for the above described analysis, but with a flow rate of 2 ml/minute. Preparative formate HPLC analysis was performed on the same type of column as the preparative phosphate analysis: solvent A was 0.01 M formic acid, containing 5 mM tetraethylammonium, pH 4.0; solvent B was as solvent A, with 50% (v/v) methanol. The elution gradient increased linearly from 100% A (for 5 minutes) to 100% B over 15 minutes, and remained at 100% B for 10 minutes. The dinucleotides were identified by comparison between their absorption spectra and those of standard compounds recorded in the instrument's memory. Quantification was achieved by integration of the chromatographic peak areas, performed by the liquid chromatograph management software.

Production and Purification of P18, P24 and P31

The cyclase purified from *A. polypoides* was used for the production of the dinucleotides for structural and functional studies. In a total volume of 0.4 ml of 10 mM Tris-HCl, pH 7.0, 0.05 mg of purified cyclase were incubated with 1 mM cADPR (or NAD$^+$), 5 mM adenine and 2 mM $MgCl_2$ at room temperature. cADPR or NAD⁺ was added to the reaction mixture every 6 hours, while every 24 hours fresh cyclase was added and an aliquot of the incubation was deproteinised with TCA (5% final concentration) and analysed by HPLC (analytical phosphate) to monitor dinucleotide production. After 3-5 days, the resulting incubation was extracted with TCA and 250 µl aliquots were injected into an HPLC column (preparative phosphate). The P18, P24 and P31 peaks were collected, lyophilised in a RotoVapor, re-dissolved in deionised water and injected into an HPLC column (preparative formate). Eluted peaks were collected, lyophilised and stored at −20° C.: no dinucleotide degradation was observed over a period of several months (approx. 6). The purified peaks produced by *Axinella* cyclase were used in in vitro experiments on the various cell types described hereinafter, for the enzymatic production of mononucleotides and nucleosides (see below), as internal and external HPLC standards to identify the dinucleotides in cell extracts, and for detecting the absorption spectra stored in the liquid chromatograph library as standards.

Digestion of the Purified Dinucleotides with Nucleotide Pyrophosphatase and Alkaline Phosphatase Purified dinucleotides were incubated in a total volume of 500 µl of 10 mM Tris-HCl, pH 8.0, in the presence of 2 mM $MgCl_2$ and 0.5 IU of nucleotide pyrophosphatase (NPP) (from *Crotalus adamanteus* venom, Sigma) at 37° C. for 5 hours. An aliquot of the incubation reaction was deproteinised using TCA (10% final concentration), the TCA was removed by extraction with diethyl ether and the mononucleotides were separated by HPLC (preparative phosphate) and collected. The remainder of the NPP incubation was adjusted to pH 9.0 by the addition of 10× concentrated alkaline phosphatase buffer (calf intestinal phosphatase, CIP, Amersham) and digested with 10 IU of recombinant CIP (Amersham) at 37° C. for 5 hours. The incubation mixture was deproteinised with TCA (as described) and the nucleosides were separated by HPLC (preparative phosphate) and collected. Mononucleotides and nucleosides obtained from different dinucleotides (P18, P24 and Ap2A) by digestion with NPP and CIP, respectively, were then subjected to preparative formate HPLC analysis, in order to remove excess phosphate: the peaks were collected, lyophilised and stored at −20° C. NPP digestion of the dinucleotides was also useful for obtaining the conversion factor between areas and nanomoles for P18 and P24 and the mononucleotides deriving therefrom, since such a digestion produces equimolar amounts of AMP (adenosine monophosphate), whose conversion factor was established with a commercially available authentic AMP sample. Commercially available Ap2A (Sigma) was used to calculate the conversion factor area/nmol for P31.

The mononucleotides and nucleosides obtained from P18 and P24, by digestion with NPP and CIP, were used in cytotoxicity experiments and for the structural analyses (UV spectrum, mass spectrum and NMR analysis).

Mass Spectrometry

P18, P24 an P31 and the mononucleotides deriving therefrom by digestion with NPP, were analysed by strong anion exchange chromatography, coupled with an ion trap mass spectrometer (1100 LC-MSD, Agilent Technologies, Palo Alto, Calif.). Chromatographic separation was obtained on a PL1000-SAX column (Hewlett-Packard) using a linear gradient from 100% water to 100% 0.3 M trifluoroacetic acid (TFA) over 20 minutes. The mass (MS) and mass/mass (MS/MS) analyses were performed on negative ions. The ion source and collision energy parameters were optimised for both the molecular ions and the fragments thereof.

NMR Spectroscopy

The iso-adenosine units obtained by alkaline phosphatase digestion of the iso-AMP units from P18 and P24 were subjected to NMR spectroscopy in order to identify the purine ring nitrogen atom involved in the glycosidic bond. The ¹H (500 MHz) and ¹³C (125 MHz) NMR spectra were obtained with a Bruker AMX-500 spectrometer.

The chemical shift values were compared to the signal of the solvent (DMSO-$d_6$: $\delta_H$=2.50; $\delta_C$=39.7). ¹H homonuclear correlations were determined with COSY experiments. ¹H—¹³C single bond correlations were determined by 2D g-HSQC pulse sequence, with a 0.50 s BIRD pulse prior to each scan, in order to suppress the signals originating from protons not directly bound to $C^{13}$ (interpulse delay per $^1J_{CH}$=125 Hz). ¹H—¹³C 2 and/or 3 bond correlations were determined by 2D HMBC experiments optimised for $^{2,3}J$ of 7 Hz.

P18 detection in HeLa Cell Extracts by Enzymatic Cycling

The presence of P18 in CD38⁺ and CD38⁻ HeLa cell extracts was investigated by exploiting the ability of *Axinella* cyclase to convert P18 to NAD⁺ in the presence of an excess of nicotinamide. The NAD⁺ concentration was thus determined by a very sensitive cyclic enzymatic assay (Graeff, R. and Lee, H. C. (2002) Biochem. J. 361, 379-384). TCA cell extracts (200 µl of the 400 µl prepared as described above) were injected in an HPLC column (analytical phosphate) and fractions were collected every minute. Fractions 16 to 20 were processed as described below in connection with P18 determinations, while fractions 21 to 25 were analysed by HPLC in order to detect the presence of P24.

In parallel with the CD38⁺ HeLa cell extract, the same volume of water (as a "background" for the enzymatic assay), a cell extract containing 1 nmole of purified P18 (in order to verify that the P18 elution time was not modified by the presence of the cell extract) and increasing amounts of P18 (for the preparation of a standard curve for the enzymatic assay) were separated by HPLC. The relevant fractions (minutes 16-20) were collected. In order to avoid contamination of the cell sample with standard P18, the HPLC analyses were performed in the following order: water, CD38⁻ cell extract, CD38⁺ cell extract, CD38⁺ cell extract containing standard P18 and finally the different amounts of standard P18.

The HPLC fractions were lyophilised, resuspended in 200 µl water and the pH eas adjusted to 7.5 with 5N NaOH. Then, in order to remove all traces of NAD⁺ and cADPR (which might interfere with the enzymatic assay), NAD-glycohydrolase (NAD-ase, from Neurospora, Sigma) (0.013 IU), recombinant CD38 (0.1 µg, provided by Prof. H. C. Lee, Minneapolis, Minn.) and 2 mM $MgCl_2$ were added to each fraction. The digestion was performed as a precautionary measure, although the cADPR (8 minutes) and NAD⁺ (15 minutes) retention times are sufficiently far from those of P18 that any contamination is unlikely. P18 resistance to NAD-ase and CD38 catalysed hydrolysis had been ascertained in advance. All fractions were incubated at 37° C. for 18 hours, and the enzymes were removed by filtration with Immobilon-P membranes (Millipore, Bedford, Mass.). The samples were then subdivided into two aliquots and the P18 determination reactions were performed in 96 well plates, at room temperature. 50 µl of a mixture containing 30 mM nicotinamide, 100 mM sodium phosphate, with or without 0.1 µg/µl of ADP-ribosyl cyclase purified from *A. polypoides*, were added to 100 µl of each sample. Finally, the assay started with the addition of the reagent (Graeff, R. and Lee, H. C. (2002) Biochem. J. 361, 379-384), allowing the determination of the NAD⁺ levels in each sample.

Figure 3:
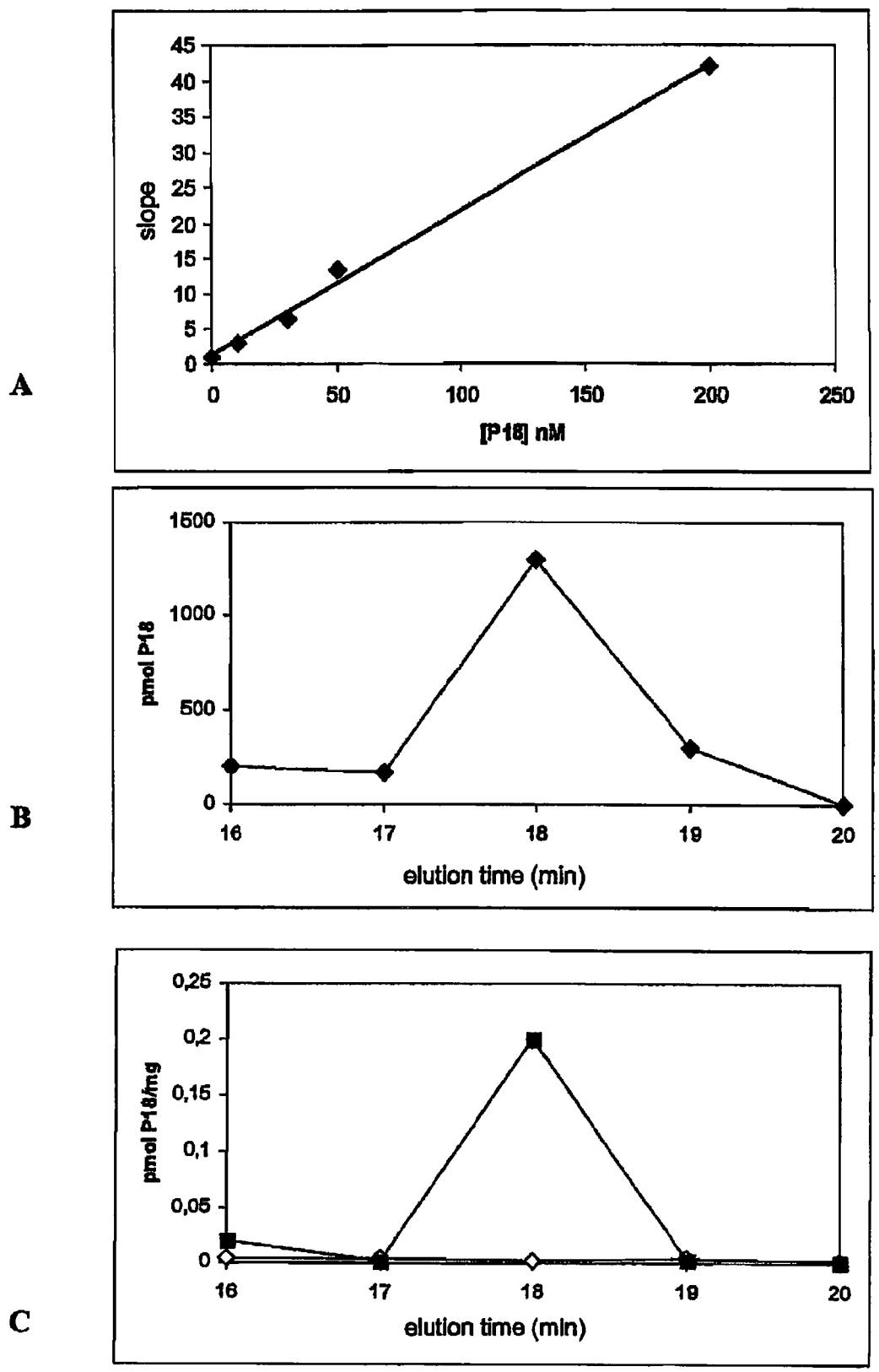
FIG. 3 shows the detection of P18 in cyclase-positive HeLa cells (CD38$^+$) by enzymatic cyclic assay. A. Standard curve, prepared with known amounts of purified P18, injected singularly onto HPLC, recovered and subjected to enzymatic assay. B. Detection of purified P18, added as an internal standard to a cyclase-negative HeLa cell extract (CD38$^-$), in HPLC fractions 18-19. C. Detection of P18 in fraction 18 of an HPLC analysis of a CD38$^+$ HeLa cell extract (■), and the absence of P18 in the CD38$^-$ HeLa cell extract (◊).

The standard curve for P18, prepared from known amounts of the dinucleotide injected in HPLC, was linear within the range between 0.5 and 200 nM P18 (FIG. 3A), indicating that the *Axinella* cyclase-mediated conversion of P18 to $NAD^+$ is efficient, also at nanomolar concentrations. The P18 added to the HeLa cell extract as an internal standard was detected in fractions 18-19 of the corresponding chromatogram (FIG. 3B), and the total detected amount of the dinucleotide was similar to the amount added to the extract.

P24 Detection in HeLa Cells by HPLC Analysis

Fractions 21 to 25 of the HPLC analyses used for detecting P18, were lyophilised and resuspended in 300 µl of water. The pH was adjusted to 7.5 with 5 N NaOH and each fraction was incubated at 37° C. for 90 minutes in the presence or absence of 0.06 IU of NPP and 2 mM $MgCl_2$. The enzyme was removed by filtration through a membrane (Millipore) and the samples were injected in an HPLC column (analytical phosphate). P24 was identified in the undigested samples by comparing the retention time and the absorption spectrum with those of a standard. Identification was confirmed by conversion of the putative P24 into the corresponding iso-AMP in a parallel sample digested with NPP.

Intracellular Calcium Assays

Adherent $CD38^+$ and $CD38^-$ human HeLa cells on 20 mm-diameter coverslips were incubated in complete medium in the presence of 1 µM P18 or P24 for 12 hours. The cells were then washed, incubated with 6 µM Fura 2-acetoxymethyl ester (FURA 2-AM) in standard saline (135 mM NaCl, 5.4 mM KCl, 1.8 mM $CaCl_2$, 1 mM $MgCl_2$, 5 mM Hepes, 10 mM glucose, pH 7.4) for 45 minutes at 37° C. and then washed several times with saline. Calcium measurements were performed in a 200-µl chamber mounted on an inverted microscope, as described in detail in Zocchi E., et al. (1998) J. Biol. Chem. 273, 8017-8024. After determination of basal $[Ca^{2+}]_i$ levels, 1 µM tapsigargine was added to induce the release of calcium from tapsigargine-sensitive stores (endothelial-reticulum). The parameter values needed for calibration were obtained at the end of the experimental measurements, as described in Zocchi E., et al. (1998) J. Biol. Chem. 273, 8017-8024.

Cell Proliferation Assays

Mononuclear cells were isolated from cord blood (CB MNC) by a density gradient, washed by centrifugation and resuspended in complete medium (Mosmann, T. (1983) J. Immunol. Methods 65, 55-63). Cells ($10^6$/ml) were incubated for 24 hours in complete medium in the presence of different dinucleotides at concentrations comprised between 20 and 0.4 µM. Then, aliquots of cells ($1-2\times10^4$) were seeded in semi-solid medium, supplemented with haemopoietic growth factors (Methocult, Stem Cell Technologies, Vancouver, BC), in order to allow colonies to develop. After 2 weeks in culture, the colonies which were grown were microscopically identified according to standard criteria (CFU-E, CFU-GM and CFU-GEM) and counted: each colony identifies a colony forming cell (CFC).

In other experiments, CB MNC were cultured in the medium conditioned by $CD38^\pm$ HeLa cells. The 3-day conditioned medium by confluent monolayers of $CD38^\pm$ HeLa cells was incubated in the absence (control) or in the presence of NPP (0.5 IU/ml) for 6 hours at 37° C. The pH of both samples was then adjusted to 9.0 with 5N NaOH and the NPP-incubated sample was digested with CIP (2 IU/ml) for 6 hours at 37° C., while the control medium was incubated for the same time without additions. Finally, the pH of both samples was adjusted to 7.5. CB MNC ($10^6$/ml) were cultured for 10 days in 70% conditioned medium plus 30% fresh medium, with one medium change after 5 days. Upon completion of the culture, aliquots of cells ($2-5\times10^4$) were seeded in semi-solid medium to assess colony growth.

The effect of P18 and P24 on the proliferation of several cell lines was determined by the MTT reduction assay (Mosmann, T. (1983) J. Immunol. Methods 65, 55-63). Briefly, cells were seeded at a concentration of $3\times10^4$/well in flat-bottomed 96-well plates and grown in complete medium in the presence of various concentrations (ranging between 20 and 0.4 µM) of purified dinucleotides. After 24 hours, 10 µl of a 5 mg/ml solution of MTT were added to each well and the plates incubated for a further 2 hours. The supernatant was then removed from each well and the blue crystals produced by the reduction of the dye were dissolved in DMSO (200 µl/well). The optical absorbance at 570 nm was determined with a BioRad microplate reader.

Results

Synthesis and Degradation of P18, P24 and Ap2A by ADP-ribosyl Cyclases from Lower and Higher Metazoa The ADP-ribosyl cyclases from *Axinella polypoides* (porifera, demospongiae), *Aplysia californica* (molluscs, nudibranchia) and the human CD38 cyclases, all produced 3 unidentified chromatographic peaks from cADPR and adenine. FIG. 1 shows representative chromatograms obtained from incubations with the ADP-ribosyl cyclases purified from *A. polypoides* (FIG. 1A), from *A. californica* (FIG. 1B), with recombinant human CD38 cyclase (FIG. 1C) and with human HeLa cells transfected with human CD38 (FIG. 1D). The dinucleotides corresponding to the peaks at 18, 24 and 31 minutes were identified as P18, P24 and P31, respectively, by their retention times. Similar chromatograms were obtained by incubation of the various cyclases with $NAD^+$ and adenine, whereas the formation of such peaks was not observed in the absence of cyclase activity (i.e. without the addition of the purified enzymes or with HeLa cells transfected with antisense CD38, FIG. 1D, dashed chromatogram). Optimal conditions for peak production were similar for the various cyclases, i.e. pH comprised between 6 and 8, preferably 7.0-7.5, and an adenine-cADPR (or adenine-$NAD^+$) stoichiometric ratio higher than or equal to 10. Several quantitative differences were observed among the various cyclases, regarding both the synthesis and the degradation of peaks 18, 24 and 31. In table 1, the absolute values of the peak-forming and -hydrolysing activities are compared with the cADPR-forming and -hydrolysing activities for each enzyme. The activities are expressed as nmol/min/mg.

TABLE 1

Synthesis and hydrolysis of P18, P24 and P31 by ADP-ribosyl cyclases from lower and higher Metazoa

| ADP-ribosyl cyclase | cADPR | P18 | P24 | P31 |
|---|---|---|---|---|
| Recombinant CD38 | 20 | 7.3 | 2.3 | 1.2 |
| | 308 | 6.0[1] | 0.25[1] | ND |
| HeLa-CD38+* (whole cells)[3] | 0.07 | 0.022 | 0.018 | 0.0017 |
| | 0.49 | 0.24[1] | 0.06[1] | 0.15 |
| *A. polypoides* | 167800 | 30.7 | 85.0 | 6.1 |
| | 170 | 10.5[2] | ND | ND |

TABLE 1-continued

Synthesis and hydrolysis of P18, P24 and P31 by ADP-ribosyl cyclases from lower and higher Metazoa

| ADP-ribosyl cyclase | cADPR | P18 | P24 | P31 |
|---|---|---|---|---|
| A. californica | 70000 | 53.5 | 44.6 | 80.3 |
| | 770 | 3.5[1] | ND | ND |

Synthesis of P18, P24 and P31 from cADPR and adenine and hydrolysis (in bold) were determined for each enzyme (recombinant CD38, CD38 expressed in human HeLa cells, purified Axinella polypoides cyclase and recombinant Aplysia californica cyclase) and compared with the corresponding cADPR (from NAD+) synthesising activities and cADPR hydrolysing activities.
[1]to adenine and ADPR;
[2]to cADPR and adenine;
[3]in cell lysates, the hydrolysis of P18 and P24 was 10-fold higher compared to whole cells; NR, not detectable.
*No synthesis or degradation detectable in CD38− HeLa cells.

The specific activity of the enzymes from invertebrates for the synthesis of CADPR (cyclase) and for the synthesis of the various peaks, is higher than the human CD38 enzyme, either recombinant or expressed in transfected cells. None of the purified cyclases is capable of hydrolysing Ap2A and P24, whereas both dinucleotides are degraded into CD38+ HeLa cells, but not into CD38− cells, with the consequent production of adenine and hypoxanthine. On the other hand, P18 is hydrolysed to yield adenine and ADPR by all the cyclases, with the exception of the Axinella cyclase which converts P18 to cADPR and adenine, a property which was used to develop an enzymatic assay method for P18 in cell extracts.

Because the activities of the various enzymes vary over a very wide range (almost 4 logs), the peak-forming activity was expressed as a percentage of the cyclase and cADPR-hydrolase activities of each cyclase (Table 2).

TABLE 2

Peak production relative to cyclase or hydrolase activity

| | P18 (% cyclase or hydrolase) | P24 (% cyclase or hydrolase) | P31 (% cyclase or hydrolase) |
|---|---|---|---|
| Recombinant CD38 | 36 | 11 | 6.0 |
| | 24 | 3.7 | 0.4 |
| HeLa-CD38+* (whole cells) | 31 | 26 | 2.4 |
| | 4.5 | 3.7 | 0.3 |
| A. polypoides | 0.02 | 0.05 | 0.004 |
| | 18 | 50 | 3.6 |
| A. californica | 0.08 | 0.06 | 0.11 |
| | 6.9 | 5.8 | 10.4 |

Production of P18, P24 and P31 from cADPR and adenine by the indicated ADP-ribosyl cyclase is expressed as a percentage of the cyclase or cADPR-hydrolase activities thereof (in bold). The results are the mean of at least 3 separate experiments: s.d. ≦ 15% of the mean value.
*No synthesis or degradation detectable in CD38− HeLa cells.

Peak formation activities correlate better with hydrolase than with cyclase activities. Indeed, the percentage values in the various enzymes vary within narrower limits (0.5-50% of hydrolase activity compared with 0.004-36% of cyclase activity). This suggests that the catalytic mechanism of peak formation is similar to hydrolysis of cADPR, with adenine substituting for water. In the presence of adenine, the production of peaks 18 and 24 is a meaningful percentage of the cyclase activity of the human CD38 enzyme, both the recombinant (36%) and the native enzyme, expressed on the membranes of transfected cells (37%).

Because of the high specific activity of the cyclase purified from A. polypoides, this enzyme was used to produce the dinucleotides required for functional and structural studies.

Determination of the Structure of P18, P24 and P31

Analysis of the UV Spectrum and the Mass Spectrum of the Nucleotide Fragments Obtained by Enzymatic Digestion of the Dinucleotides HPLC purified peak 31 co-eluted with a diadenosine pyrophosphate (Ap2A) standard its UV spectrum was identical to that of Ap2A. For this reason, it was tentatively identified as Ap2A (Ap2A*). P18 and P24 were sensitive to acid hydrolysis, yielding adenine and ADPR, identified by their HPLC co-elution and UV spectrum identity with the relevant standards. Such elements suggested the presence of an unusual, acid-labile, N-glycosidic bond in the P18 and P24 structures.

P18, P24 and P31, produced by incubation of Axinella cyclase with CADPR and adenine and purification by HPLC, were digested with nucleotide pyrophosphatase (NPP). The digestion products were separated by HPLC. Digestion of P18 with NPP produced a peak at 8 minutes (P8) and a peak which co-eluted with, and which had the same UV spectrum as, the AMP standard, and which was tentatively identified as AMP (AMP*). Digestion of P24 produced a peak at 11 minutes (P11) and AMP*. Finally, hydrolysis of P31 produced AMP* alone, consistently with its identification as Ap2A. Such results demonstrate the dinucleotide structures of P18, P24 and P31. The nucleotides obtained from digestion of P18, P24 and P31 with NPP were subjected to UV and mass spectroscopy.

Comparison of the UV spectra (at pH 5) of the mononucleotides derived by P18, P24 and P31 digestion with NPP showed λmax values of 260 nm for AMP*, 264 nm for P8 and 274 nm for P11, similar to those reported for N9-methyl-adenine and the isomers thereof, N1-methyl-adenine and N3-methyl adenine, respectively (Fujii, T. and Itaya, T. (1999) Heterocycles 51 (9), 2255-2277). The pH is known from the literature to differently modify the absorbance spectra of the various isomers of methyl-adenine: while the λmax value of N1-methyl-adenine changes considerably between pH 5 and pH 11, the λmax of N9-methyl-adenine and of N3-methyl-adenine remain unchanged (Fujii, T. and Itaya, T. (1999) Heterocycles 51 (9), 2255-2277). Thus, the effect of pH on the λmax values of P8, P11 and AMP* was compared. While the λmax value of P8 shifted from 264 nm at pH 5 to 272 nm at pH 11, the λmax value of P11 remained unchanged (at 274 nm) at all pH values, as did the λmax value of AMP* and of standard AMP (at 260 nm). Such results were consistent with the hypothesis that P8 and P11 are N1-isoAMP and N3-isoAMP, respectively.

Mass spectrometry analysis of the products of NPP digestion of P18, P24 and P31 yielded an identical mass (m/z) of 346.6 for each mononucleotide (P8, P11 and AMP*), identical to that of standard AMP. Moreover, the mass of the dinucleotides was identical to that of standard Ap2A (m/z 675.3). Thus, based on such results, P31 can be identified as Ap2A, because of the identity of mass, HPLC retention time and the absorbance spectrum of the dinucleotide, and of the mononucleotide obtained by enzymatic digestion, with the relative standard (Ap2A and AMP). P18 and P24 are isomers of Ap2A, where one of the N-glycosidic bonds between adenine and ribose is different from the usual N9, probably involving N1 in P18 and N3 in P24.

The area of the HPLC peaks of known quantities of AMP standard has been used to calculate the conversion factor between area and nanomoles for P18 and P24 and for the iso-AMP isomers derived therefrom by digestion with NPP.

NMR Analysis

To identify the nitrogen atom involved in the N-glycosidic bond in the iso-AMP isomers obtained by NPP digestion of P18 and P24, mononucleotides P8 and P11 were dephosphorylated to obtain the corresponding nucleosides to be subjected to spectroscopic analysis.

Both P8 and P11 proved to be resistant to 5'-nucleotidase (which conversely dephosphorylates AMP), while they were substrate of alkaline phosphatase (CIP). Thus, NPP digestion of P18 and P24, followed by treatment with CIP, produced two nucleosides for each dinucleotide, as indicated below:

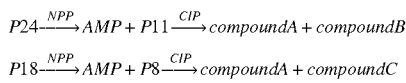

$$P24 \xrightarrow{NPP} AMP + P11 \xrightarrow{CIP} compound A + compound B$$
$$P18 \xrightarrow{NPP} AMP + P8 \xrightarrow{CIP} compound A + compound C$$

Compound A were easily identified as adenosine because its $^1H$ and $^{13}C$ spectra were identical to those of a sample of standard adenosine. On the other hand, the $^1H$ and $^{13}C$ spectra of compound B were different from the corresponding spectra of compound A, and were similar to those reported in the literature for 3-iso-adenosine(3-β-ribofuranosyladenine). Unfortunately, the NMR spectra reported in the literature for 3-iso-adenosine are incomplete and, in some cases, contradictory, probably due to the effect of pH and changes in the concentration on NMR resonance. Thus, a detailed 2D NMR analysis was necessary to unambiguously define the chemical structure of compound B.

Thus, the 2D $^1H$—$^1H$ COSY spectrum, whose cross peaks correlate protons showing scalar coupling, was instrumental to assign the proton resonances of the sugar spin systems, while the g-HSQC spectrum allowed the association of the proton resonances with those of the directly attached carbon atoms. Finally, the HMBC experiment, showing correlation peaks in corresponance of proton and carbon atoms separated by two or three bonds, provided essential information to clarify the chemical structure of compound B. Particularly, the key HMBC $^3J_{H—C}$ correlations H-8/C-5 and H-2/C-6 and those of the anomeric proton H-1' with C-2 and C-4 are unambiguously indicative of the linkage of the sugar at N-3, thus demonstrating the 3-iso-adenosine nature of compound B. The complete NMR $^1H$ and $^{13}C$ assignments for compound B are reported in Table 3.

Figure 2:
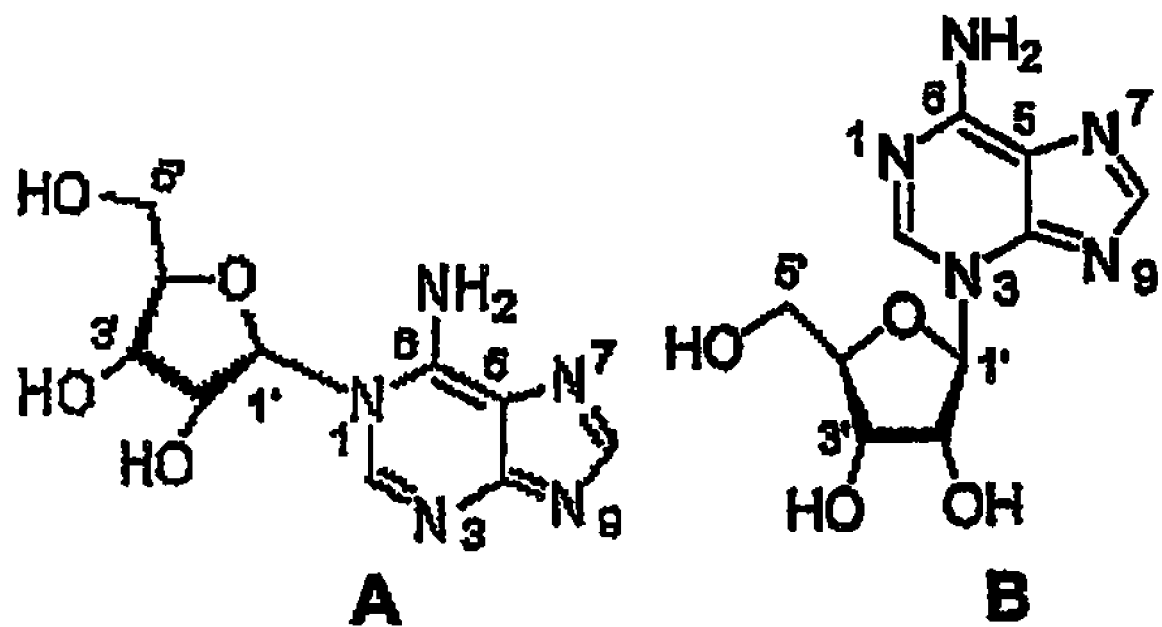
FIG. 2 shows the structure of the iso-adenosine units resulting from the digestion of P18 and P24 with NPP and CIP. A=N1-iso-adenosine, from P18; B=N3-iso-adenosine, from P24.

A similar approach was also used to deduce the structure of compound C, obtained by digestion of P18 with NPP and CIP and separation of the products by HPLC. The NMR $^1H$ and $^{13}C$ spectra of compound C were different from those of compounds A and B and thus, also in this case, study of the structure was guided by inspection of the 2D NMR spectra. Particularly, the g-HSQC spectrum allowed the association of all of the proton resonances (the carbohydrate signals and the two singlets at δH 7.66 and 7.21) with those of the relevant carbon atoms. On the other hand, the HMBC $^3J_{H—C}$ correlations H-2/C-6, H-8/C-4, H-8/C-5 and those of the anomeric proton H-1' with C-2 and C-6 indicated the linkage of the sugar moiety on N-1. Since the sugar moiety was identified as β-ribofuranose based on comparison of the NMR data with those reported in the literature, compound C must be 1-iso-adenosine(1-β-D-ribofuranosyladenine). The isolation of 1-iso-adenosine is a particularly remarkable result, since this molecule had never been described before, neither in a biological material nor as a result of a synthetic process. The complete NMR assignments for 1-iso-adenosine are reported in Table 3. The deduced structures of the iso-adenosine units contained in P18 and P24 are reported in FIG. 2.

TABLE 3

NMR data for compounds B and C, recorded in DMSO-$d_6$.[a]

| | B | | C | |
|---|---|---|---|---|
| Pos. | δC, mult. | δH, mult., J in Hz | δC, mult. | δH, mult., J in Hz |
| 2 | 144.0 CH | 8.33, s | 140.5, CH | 7.66, s |
| 4 | 148.4 C | | 151.8, C | |
| 5 | 121.6 C | | 122.9, C | |
| 6 | 155.6 C | | 157.3, C | |
| 8 | 152.1 CH | 7.76, s | 148.6, CH | 7.21, s |
| 1' | 95.9 CH | 5.87, d, 6.8 | 93.4, CH | 5.73, d, 6.8 |
| 2' | 74.0 CH | 4.75, dd, 6.8, 6.0 | 72.0, CH | 4.61, dd, 6.8, 6.0 |
| 3' | 74.8 CH | 4.15, dd, 6.0, 2.5 | 71.1, CH | 4.01, dd, 6.0, 3.0 |
| 4' | 85.8 CH | 4.08, bd, 2.5 | 86.5, CH | 3.93, bd, 3.0 |
| 5'a | 61.7 CH$_2$ | 3.70, bd, 12.2 | 61.8, CH$_2$ | 3.56, bd, 12.5 |
| 5'b | | 3.57, bd, 12.2 | | 3.46, bd, 12.5 |

[a] the $^{13}C$ assignments are based on HSQC and HMBC data

Metabolism and Presence of P18, P24 and Ap2A in Cyclase-positive Cells

In CD38⁻ cells, uptake of extracellularly added P18, P24 and Ap2A (15 μM) occurs. Their intracellular concentration is undetectable at zero time and increases with the incubation time at a rate of approx. 2.4 pmol/min/mg, which is similar for all the different dinucleotides. Intact CD38⁺ cells hydrolyse P18, P24 and Ap2A with extracellular production of adenine and hypoxanthine. ADPR was not detectable, probably because of its rapid uptake and recycling in the adenylic nucleotide pool. In CD38⁺ cell lysates, the degradation of dinucleotides occurs at a 20-fold higher rate than in intact cells, but yields the same products (adenine and hypoxanthine) together with 3-isoAMP (from P24). These results indicate that P18, P24 and Ap2A can cross the plasma membrane of intact cells and that the unusual N-glycosidic bonds present in P18 and P24 are hydrolysed, both intracellularly and extracellularly. The fact that recombinant CD38 does not hydrolyse Ap2A might be due to structural differences between the purified enzyme and the enzyme expressed in transduced cells (the former is not glycosylated and lacks the transmembrane portion and the short intracellular domain) or might be due to the presence, in CD38⁺ cells, of other enzymes induced by the expression of CD38 and active on the dinucleotides. This seems to be confirmed by the presence of 3-isoAMP in lysates from CD38⁺ but not CD38⁻ cells, incubated with P24, indicating the presence of pyrophosphatase activity, unknown for CD38. Interestingly, 3-isoAMP is resistant to 5'-nucleotidase but is a substrate of myokinase, which phosphorylates it in the presence of ATP to the corresponding nucleotide phosphate, suggesting the possibility of a 3-iso-AMP metabolism in CD38⁺ cells.

*Axinella polypoides* cell lysates also showed pyrophosphatase activity on P24 and a hydrolyzing activity on Ap2A, with the production of adenine and ADPR, while purified cyclase does not show any hydrolyzing activity on these dinucleotides. This suggests the presence in sponge cells of other enzymes active on such dinucleotides. The synthesis and degradation, i.e. the metabolism, of P18, P24 and Ap2A added exogenously to cyclase-positive sponge and mammalian cells prompted the inventors to search for the presence of these dinucleotides in said cells.

P18, P24 and Ap2A were detected at concentrations of 0.32±0.06, 1.79±0.2 and 0.15±0.02 nmol/mg, respectively, (mean±s.d. from 3 experiments) in acid extracts from *A. polypoides* cells. The peaks isolated by HPLC were identified by comparison of retention times and absorbance spectra with the relevant standards (obtained using the purified *Axinella* enzyme) and by HPLC separation of the NPP digestion products thereof. Said concentrations are within the same order of magnitude as the cADPR concentration in *A. polypoides* cells (0.24±0.06 nmol/mg).

P24 was also detected by HPLC in the acid extract from human CD38+ HeLa cells, but not in CD38− HeLa cells, at a concentration of 9.8±0.9 pmol/mg, a value within the same order of magnitude as the cADPR concentration (50±0.2 pmol/mg). The identification of P24 was simplified by the peculiar UV spectrum of the dinucleotide and of the 3-iso-AMP derived therefrom by NPP digestion. The positive identification of P18 in CD38+ HeLa cells proved more difficult, probably due to its lower concentration compared to P24. Thus, another strategy was used. The enzymatic "cycling" assay described in the literature for cADPR (Graeff, R. and Lee, H. C. (2002) Biochem. J. 361, 379-384) was modified taking advantage of the ability of the *Axinella* cyclase to convert P18 to cADPR and adenine, and then to convert cADPR to NAD+, in the presence of excess nicotinamide (similarly to *Aplysia* cyclase), as well as of the resistance of P18 to NAD-ase P18 was detected in acid extracts from CD38+ HeLa cells, but not from CD38− cells, at a concentration of 0.14 pmol/mg, a concentration 40-fold lower than that of P24. The reason for this may lie in the higher pyrophosphatase activity expressed by CD38+ cells on P18 compared with P24.

Ap2A had been previously described in platelet secretory granules (Jankowski J., et al. (2001) J. Biol. Chem. 23, 8904-8909) and in rat cardiac myocytes (Luo J., et al. (1999) FASEB J. 13, 695-705). Notably, both cell types are cyclase-positive. The reduced Ap2A synthesising activity expressed by CD38 may be the reason why it was not possible to detect the presence of this dinucleotide in CD38+ HeLa cells.

Effects of P18 and P24 on $[Ca^{2+}]_i$ of CD38+ and CD38− HeLa Cells

In cyclase-positive sponge and mammalian cells, cADPR synthesis is accompanied by the production of P18 and P24. This prompted the inventors to study their effects on intracellular calcium, in the presence or in the absence of cADPR. The CD38± HeLa cell experimental system was used.

Basal cytosolic calcium and tapsigargine-induced release of calcium from endothelial-reticulum (ER) stores (in bold in Table 4) were measured in CD38+ and CD38− HeLa cells loaded with FURA 2-AM and incubated in the absence (control) or in the presence of P18 or P24 at a concentration of 10 μM for 18 hours. The results obtained, expressed as $[Ca^{2+}]_i$ nanomolarity, are summarised in Table 4, showing mean results from 8 separate experiments (s.d.≦15% of the mean value).

TABLE 4

Effects of P18 and P24 on the concentration of cytosolic free calcium and on the calcium content of tapsigargine-sensitive stores of human CD38+/− HeLa cells

| | Control | P18 | P24 |
|---|---|---|---|
| | | $[Ca^{2+}]_i$ nM | |
| CD38+ HeLa | 37 | 16 | 57 |
| | 254 | 123 | 203 |
| CD38− HeLa | 23 | 12 | 44 |
| | 470 | 366 | 290 |

In CD38+ cells, $[Ca^{2+}]_i$ is 60% higher, and the ER stores contain 50% of the calcium compared with CD38− cells, owing to the calcium-mobilising effect of cADPR, and consistently with previously reported results (Zocchi E., et al. (1998) J. Biol. Chem. 273, 8017-8024). Incubation with 10 μM P18 for 18 hours induces a decrease of basal $[Ca^{2+}]_i$ (41% of the control) and ER stores-calcium (48%), which is more pronounced in CD38+ HeLa cells compared with CD38− cells (52% and 78% of the control value, respectively).

Conversely, P24 induces an increase in basal $[Ca^{2+}]_i$, which was higher in CD38− cells than in CD38+ cells (191% vs. 154%), accompanied by a partial depletion of ER stores, also more pronounced in CD38− cells (60% vs. 80% in CD38+ cells). Increased $[Ca^{2+}]_i$ observed immediately following the addition of P24 (50 μM) to intact CD38[35] HeLa cells is hindered by extracellular EGTA. This indicates that the dinucleotides cause an influx of extracellular calcium, which in turn induces the release of intracellular calcium, justifying the partial depletion of calcium from the stores. The effects of P24 are more pronounced in CD38− cells, possibly because of the absence of intracellular degradation.

Conversely, P18 reduces cytosolic calcium and depletes calcium from stores. Since mitochondrial calcium does not seem to be increased by P18 in CD38± HeLa cells, these results suggest a general depletion of cellular calcium, possibly because of the stimulation of membrane ATP-ase, to which the cell responds with increased calcium release from stores, ultimately resulting in their depletion. CD38+ cells appear to be more sensitive to the effects of P18-induced depletion of stores than CD38− cells (Table 3), possibly because of the simultaneous calcium-mobilising action of cADPR.

Effects of P18 and P24 on the Proliferation of Human Haemopoietic Precursors

Figure 4:
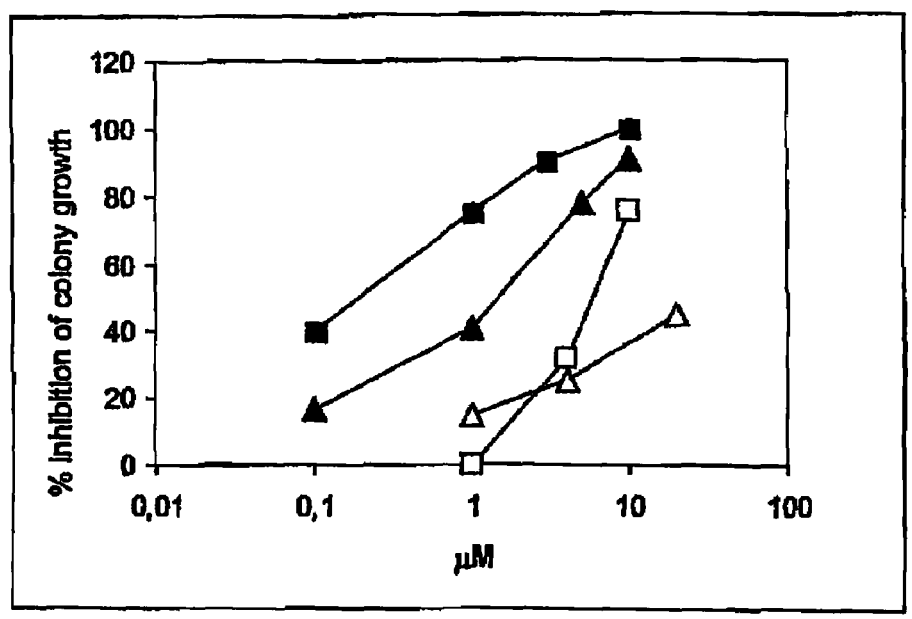
FIG. 4 shows the effects of P18 and P24 and of their respective iso-adenosines on the growth of CFC (colony forming cells). Mononuclear cells isolated from cord blood were incubated in the presence of various concentrations of P18 (▲), P24 (■) and the iso-adenosine units resulting from the enzymatic digestion of P18 (Δ) and P24 (□). After 24 hours, aliquots of cells ($1-2\times10^4$) were seeded in semi-solid medium to allow for colony growth. Results are expressed as percentage of inhibition of colony growth compared with controls, represented by cells incubated with the same dilution of chromatographic buffer as present in the HPLC-purified compounds. The $IC_{50}$ values were obtained from the logarithmic regression curves ($R \geq 0.97$). The results shown in this figure are the mean from at least three different experiments.

Finally, a study on the functional effects of dinucleotides P18 and P24 of the invention on human HP proliferation in vitro was conducted. P18 and P24 markedly inhibit CFC growth, with $IC_{50}$ values of 1.0 and 0.18 μM, respectively (FIG. 4). The iso-AMP units display similar toxicity to that of the parent dinucleotides, while the corresponding iso-adenosines are much less toxic (FIG. 4): the $IC_{50}$ values are 37 and 5 μM for the iso-adenosine from P18 and from P24, respectively. Prolonging the cells exposure time to dinucleotides increases toxicity. For example, the $IC_{50}$ of P18 is 30 μM with 2 hours of incubation and 1 μM with 24 hours of exposure. This suggests slow influx of the dinucleotides into the sensitive cells. Excess adenosine (200-fold with respect to the dinucleotides) does not protect against the toxicity of the dinucleotides, suggesting that the toxic effect is not due to an antimetabolic effect of the iso-AMP or iso-adenosine units deriving from the dinucleotides.

Toxicity of P18 and P24 was also measured on some human tumour cell lines. The cell lines of haematological origin (HL60 and K562) are slightly less sensitive than CFC to P18 and P24 (the $IC_{50}$ values are 5-40-fold higher), but much more sensitive than tumour lines of non-haematological origin, where the $IC_{50}$ values are 50-200-fold higher than those of CFC (Table 4). No significant differences were observed in the sensitivity of human CD38+ and CD38− HeLa cells, suggesting that cADPR (which is present only in cyclase-positive cells) does not protect against the toxic effects of P18 and P24. These results suggest a peculiar sensitivity of the cells having haemopoietic origin, particularly CFC, to the toxic effects of P18 and P24.

TABLE 4

$IC_{50}$ values of P18 and P24 on various human cell lines.

| Cell type | P18 $IC_{50}$ µM | P24 |
|---|---|---|
| HL60 Promyelocytic leukemia | 26 | 2.0 |
| K562 Proerythroblastic leukemia | 44 | 5.8 |
| CD38+ HeLa Ovarian carcinoma | 120 | 9.1 |
| CD38− HeLa | 150 | 9.8 |
| HCT-8 Colon carcinoma | 65 | 27.0 |
| HEP-G2 Hepatocarcinoma | 78 | 18.2 |

Figure 5:
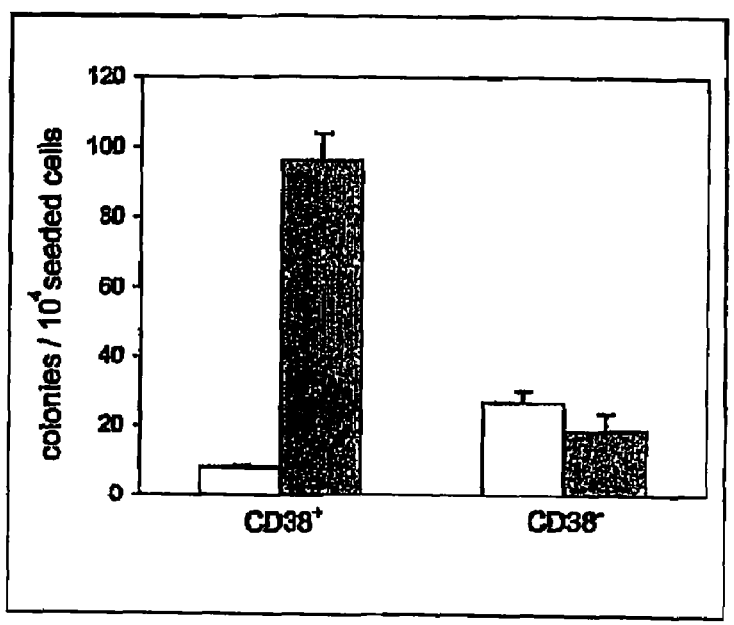
FIG. 5 shows that NPP and CIP digestion of the medium conditioned by CD38$^+$ HeLa cells removes the cytotoxic effect on CFC. The medium conditioned for 3 days from confluent monolayers of CD38$^\pm$ HeLa cells was incubated in the absence (control, white histograms) or in the presence of NPP and CIP (grey histograms). Mononuclear cells isolated from cord blood ($1\times10^6$/ml) were incubated for 10 days in 70% conditioned medium (30% fresh medium), with one medium change after 5 days. Aliquots of cells ($1-2\times10^4$) were then seeded in semi-solid medium and colony growth was estimated after 2 weeks.

In these experiments, cells were seeded onto 96 well plates ($3 \times 10^4$ cells per well) and incubated in the presence of increasing concentrations of P18 or P24. After 24 hours, the percentage of viable cells was evaluated by spectrophotometric measurement of the concentration of reduced MTT (see Materials and Methods). The means of at least three separate experiments are shown (s.d.≦20% of the mean value). The production of P18 and P24 by human CD38 cyclase, with inhibitory effects on colony growth, together with cADPR, with stimulatory effect, may be at least partly responsible for the colony growth inhibition observed during long term culture of human HP cells on CD38+ stroma. To test this hypothesis, we took advantage of the observation that digestion with NPP and CIP substantially reduces the toxicity of P18 and P24 (40 and 30-fold, respectively, FIG. 4) whereas cADPR is resistant to such enzymes. Cord blood mononuclear cells (CB MNC) were cultured for 2 weeks in medium conditioned (CM) by human CD38+ or CD38− HeLa cells, previously subjected to enzymatic digestion with NPP and CIP. The development of colonies from HP cells cultured in CD38+ conditioned medium, treated with enzymes, is increased 10-fold compared to that of HP cells cultured in CD38+ conditioned medium untreated with enzymes, and 5-fold compared to that of HP cells cultured in CD38− conditioned medium treated with enzymes (FIG. 5). Thus, enzyme digestion of CD38+ conditioned medium has revealed a stimulatory effect on CFC growth. These observations suggest that toxic dinucleotides are involved in the inhibitory effect of CD38+ CM on CFC, an effect which had previously been attributed to the secretion of interferon-γ by the CD38+ stroma. This observation may be clinically relevant, in that infiltration of the haemopoietic bone marrow by activated lymphocytes (CD38+) has been proposed as the pathogenic mechanism of bone marrow failure syndromes (aplasia and graft rejection).

In conclusion, the studies illustrated herein showned that ADP-ribosyl cyclases (E.C. 3.2.2.5) produce three adenyl dinucleotides from cADPR and adenine: Ap2A and two isomers thereof, known as P18 and P24 based on their HPLC retention times. Conservation of this catalytic property from lower Metazoa to higher Metazoa suggests that such molecules play an important physiological role, such as that observed for CADPR. The Ap2A isomers contain an unusual N-glycosidic bond (C1-N1 in P18 and C1-N3 in P24) and represent the first example of adenyl dinucleotide isomers produced in animal cells. Said dinucleotides share certain properties: (i) they are present and metabolised in cyclase-positive cells, but not in cyclase-negative cells, and (ii) they affect $[Ca^{2+}]_i$ and cell proliferation in both cell types. The cytotoxic activity of the Ap2A isomers P18 and P24 on a number of human tumour cell lines was also demonstrated. The peculiar sensitivity of human haemopoietic precursors and of a number of tumour cell lines of haematological origin, opens the way for the use of P18 and P24 as active ingredients in antitumour medicaments, particularly for neoplastic diseases of haematological origin, such as for example leukemias and lymphomas.

Thus, a pharmaceutical composition comprising dinucleotide P18 and/or dinucleotide P24 as the active ingredient, and a pharmaceutically acceptable carrier, falls within the scope of the present invention. The compositions of the present invention are preferably administered parenterally. The composition is prepared in a unit dosage form adapted for the selected mode of administration, for example by intravenous injection. In this case, any sterile saline solution may be used as a pharmaceutically acceptable carrier. The concentration of the active ingredient in the composition may vary within a wide range, for example from 1 to 500 mM, preferably from 50 mM to 100 mM. A preferred concentration is 50 mg/ml. The composition may further contain additional ingredients such as excipients, pH regulators, salts, buffers etc. The selection of type and the quantity of such additional ingredients falls within the ability of one skilled in the art, and does not require the practice of any inventive activity nor any experiments exceeding normal routine experimentation.

Finally, the inventors observed that ADP-ribosyl cyclase derived from *Axinella* is capable of converting the dinucleotide P18 into NAD+ in the presence of excess nicotinamide. This property was used to develop a method for enzymatically assaying P18 in a biological sample, for example on cell extracts containing the dinucleotide P18, or suspected of containing said dinucleotide. Thus, also within the scope of the invention is a method for enzymatically assaying P18 in a biological sample, comprising the steps of: (i) converting P18 into NAD+ by incubation of the biological sample with *Axinella polypoides* ADP-ribosyl cyclase in the presence of excess nicotinamide, and (ii) enzymatically assaying NAD+ on said biological sample with any suitable method. Since the conversion of P18 into NAD+ is complete in the presence of excess nicotinamide, the amount of NAD+ thus determined is indicative of the amount of P18 in the biological sample.

The invention claimed is:

1. An isolated compound selected from dinucleotide P18 of formula (I) or dinucleotide P24 of formula (II):

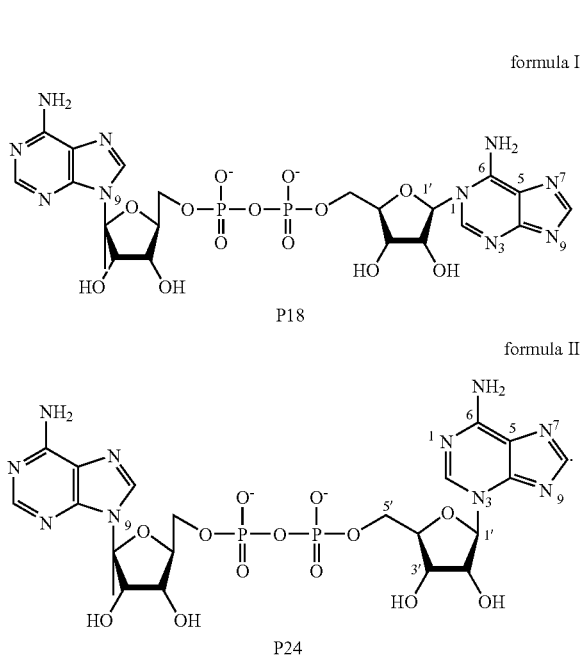

2. A pharmaceutical composition comprising: an active ingredient, said active ingredient being isolated dinucleotide P18 of formula (I) or isolated dinucleotide P24 of formula (II);

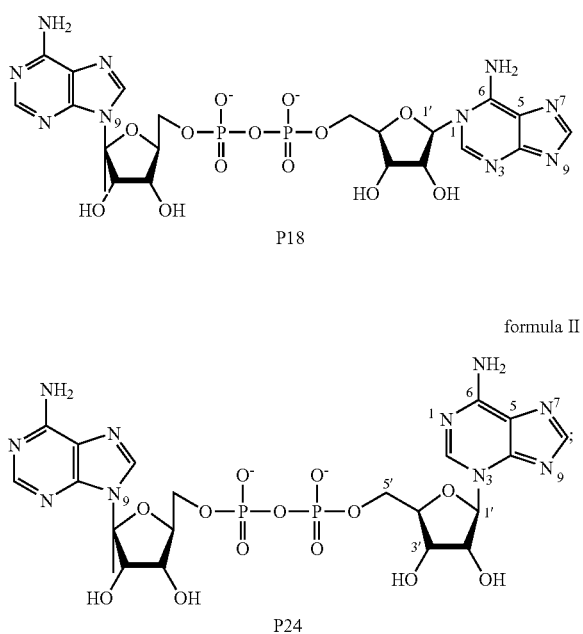

and a pharmaceutically acceptable carrier.

3. A method for preparing dinucleotide P18 of formula (I) or dinucleotide P24 of formula (II)

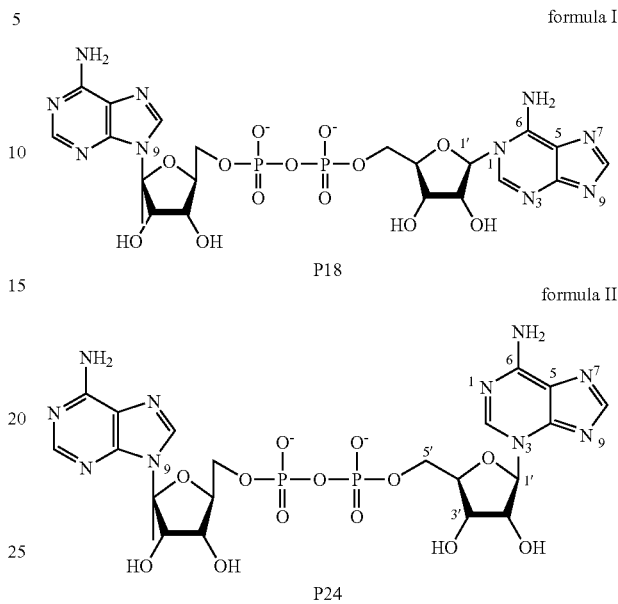

comprising the steps of:
   (i) incubating cyclic-ADP-ribose or NAD$^+$ with adenine in the presence of ADP-ribosyl cyclase at a pH of approximately 6 to 8, thereby obtaining a mixture of products comprising P18 of formula (I) and P24 of formula (II), and
   (ii) separating P18 of formula (I) and/or P24 of formula (II) from said mixture.

4. The method according to claim 3, wherein said ADP-ribosyl cyclase is *Axinella polypoides* ADP-ribosyl cyclase, *Aplysia californica* ADP-ribosyl cyclise or human CD38 cyclase.

5. A method for enzymatically assaying P18 of formula (I):

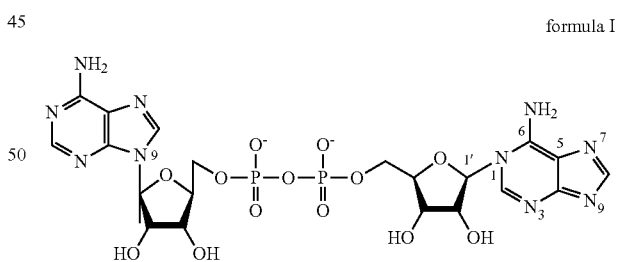

within a biological sample, comprising the steps of:
   (i) converting P18 of formula (I) into NAD$^+$ by incubating said biological sample with ADP-ribosyl cyclase in the presence of an excess of nicotinamide, and (ii) enzymatically assaying NAD$^+$ on said biological sample, the amount of NAD$^+$ being indicative of the amount of P18 of formula (I).

6. The method according to claim 5, wherein said ADP-ribosyl cyclase is *Axinella polypoides* ADP-ribosyl cyclise or *Aplysia californica* ADP-ribosyl cyclase.

7. A method of therapeutically treating a subject affected by leukemia or lymphoma, comprising administering to said subject a therapeutically effective amount of isolated dinucleotide P18 of formula (I) or isolated dinucleotide P24 of formula (II):
formula I
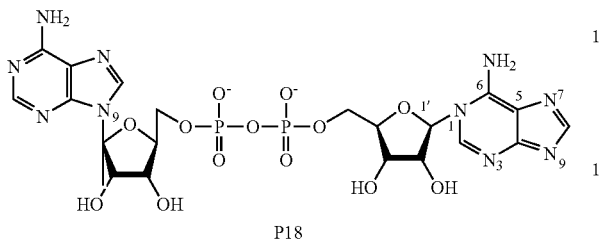
P18
-continued
formula II
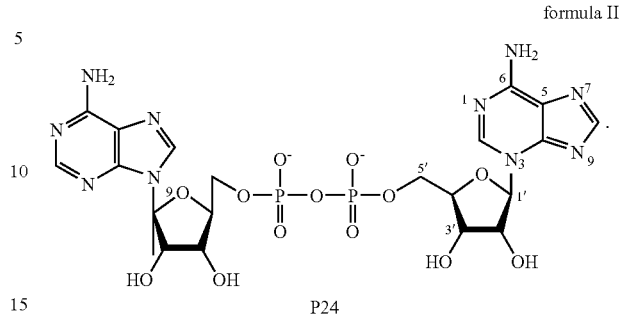
P24
* * * * *